United States Patent
Carney

(10) Patent No.: US 9,150,756 B2
(45) Date of Patent: Oct. 6, 2015

(54) SAMPLING DEVICE FOR SUBSTANCE DETECTION INSTRUMENT

(75) Inventor: Kenneth Carney, Rancho Cucamonga, CA (US)

(73) Assignee: HAMILTON SPACE SYSTEMS INTERNATIONAL, INC., Windsor Locks, CT (US)

( * ) Notice: Subject to any disclaimer, the term of this patent is extended or adjusted under 35 U.S.C. 154(b) by 763 days.

(21) Appl. No.: 13/207,071

(22) Filed: Aug. 10, 2011

(65) Prior Publication Data

US 2013/0036836 A1 Feb. 14, 2013

(51) Int. Cl.
- *G01N 30/96* (2006.01)
- *C09D 183/14* (2006.01)
- *G01N 1/02* (2006.01)
- *C08G 77/52* (2006.01)

(52) U.S. Cl.
CPC ............. *C09D 183/14* (2013.01); *G01N 1/02* (2013.01); *C08G 77/52* (2013.01); *G01N 2001/028* (2013.01); *Y10T 428/249991* (2015.04)

(58) Field of Classification Search
CPC ......... G01N 1/02; G01N 1/22; G01N 1/2214; G01N 2001/028
USPC ............ 422/69, 83, 88, 89, 534, 535; 96/108, 96/109, 121
See application file for complete search history.

(56) References Cited

U.S. PATENT DOCUMENTS

| | | |
|---|---|---|
| 3,671,489 A | 6/1972 | Barnes et al. |
| 3,959,403 A | 5/1976 | LaRochelle |
| 4,145,504 A | 3/1979 | Hedaya et al. |
| 4,208,492 A | 6/1980 | Hedaya et al. |
| 4,235,987 A | 11/1980 | Peters |
| 4,433,982 A | 2/1984 | Odernheimer et al. |
| 4,444,662 A * | 4/1984 | Conover .................. 210/500.36 |
| 4,541,268 A | 9/1985 | Odernheimer |
| 5,019,139 A | 5/1991 | LaPack et al. |
| 5,208,310 A | 5/1993 | Dougherty |
| 5,212,991 A | 5/1993 | Suzanne et al. |
| 5,324,938 A * | 6/1994 | Hambitzer et al. ........... 250/288 |
| 5,346,980 A | 9/1994 | Babu |
| 5,448,062 A * | 9/1995 | Cooks et al. .................. 250/288 |
| 5,517,026 A | 5/1996 | Sickenberger et al. |
| H1612 H | 11/1996 | Rhein et al. |
| 6,444,326 B1 | 9/2002 | Smith |
| 6,511,760 B1 | 1/2003 | Barone et al. |
| 7,070,833 B2 | 7/2006 | Smith et al. |
| 7,385,191 B1 | 6/2008 | McMurtry et al. |
| 7,579,587 B2 | 8/2009 | Krogh et al. |
| 7,867,627 B2 | 1/2011 | Smith et al. |
| 2002/0013441 A1 | 1/2002 | Muller et al. |
| 2004/0259265 A1 * | 12/2004 | Bonne ........................ 436/151 |
| 2005/0171317 A1 | 8/2005 | Keller et al. |

OTHER PUBLICATIONS

Thiokol Chemical Corporation, "Carborane-Siloxane Elastomers," RMD Report 5065-Q2, pp. 1-14 (1965).

* cited by examiner

*Primary Examiner* — Jill Warden
*Assistant Examiner* — Dwayne K Handy
(74) *Attorney, Agent, or Firm* — Cantor Colburn LLP

(57) ABSTRACT

A sampling device for a substance detection instrument includes
- a membrane comprising a porous support having a coating thereon, the coating comprising a carborane polysiloxane or an arylene polysiloxane, the membrane having a front side configured to be placed in contact with a test sample and a back side;
- a sample line having an inlet proximate to the back side of the membrane and an outlet in fluid communication with a substance detector; and
- a source of carrier gas in fluid communication with the back side of the membrane and the sample line inlet.

17 Claims, 3 Drawing Sheets

SAMPLING DEVICE FOR SUBSTANCE DETECTION INSTRUMENT

STATEMENT OF GOVERNMENT INTEREST

This invention was made with government support under W911SR-10-D-001 awarded by the United States Army. The government has certain rights in the invention.

BACKGROUND OF THE INVENTION

Often it is important to quickly and accurately determine the level and type of chemical compounds present on the surface of a material. For example, it may be desirable to quickly and reliably test for the presence of toxic industrial compounds (TICs), illegal drugs, explosive compounds, or chemical or biological weapons or substances. Some substances have a fairly high volatility. Many TICs have ambient temperature vapor pressures greater than 0.5 T (mmHg). Others, for example various explosives such as nitroglycerin, trinitrotoluene (TNT) and ethylene glycol dinitrate (EGDN), have ambient temperature vapor pressures below 0.05 T.

Various technologies have been proposed for surface contamination sampling. For example, mass spectrometry has long been used to accurately determine the presence of initially unknown chemical and biological samples. Usually a sample is vaporized for transport via gas phase flow to the analyzer and ionized, with the resulting ions being measured to determine a mass to charge ratio spectrum which is, in turn, used to identify the basic constituents of the original sample. Due to the large size and power requirements of most mass spectrometers, they have typically been housed in a dedicated laboratory. As such, samples were collected at a potentially contaminated site and brought to the mass spectrometer for analysis. This tended to be a time consuming and expensive endeavor, especially if the surface being analyzed was located a distance from the laboratory.

In order to address the problem of analyzing samples at a contamination site, portable field detection systems have been developed. For example, Bruker Daltonics manufactures portable mass spectrometers such as the MM series and the EM series. With some mass spectrometers, a sample to be tested is collected and placed in a test chamber, where it is exposed to heat and a carrier gas to volatilize and transport molecules to a mass spectrometer detection unit. Other mass spectrometers, such as Bruker Daltonics MM1 and MM2 models, utilize a sampling head or probe that is brought into contact or proximity with a surface to capture volatilized molecules from the surface and transport them to a substance detector such as a mass spectrometer. Various sampling heads or probes have been proposed in the art, see U.S. Pat. No. 4,433,982, U.S. Pat. No. 4,541,268, and/or U.S. Pat. No. 5,517,026. Such sampling heads utilize a membrane that is permeable to the volatile molecules of interest, and apply heat to the membrane when it is placed in contact or proximity to the surface being tested in order to assist in volatilization of the molecules so that they diffuse into the membrane. A carrier gas on the back side of the membrane then carries the volatile molecules to a substance detector such as a mass spectrometer. Known sampling heads, however, have limitations on their operating temperature ranges, particularly on the upper end, which limits their effectiveness on testing for a wide variety of substances potentially of interest, especially substances with low vapor pressures, and/or their use for testing high temperature surfaces. Attempts have been made to enhance the ability of silicone sampling membranes by incorporating fillers such as ferric oxide into the polymer matrix; however, this can have deleterious effects on product performance such as imputing reactivity and/or reducing analyte throughput for some analytes. Additionally, the effectiveness of transmission through the membrane is a function of analyte vapor pressure, analyte solubility in the membrane material and analyte mobility through the membrane material. All of these properties are, in turn functions of temperature and obtaining optimum, or even satisfactory, performance over a wide range of analyte volatility has been impracticable.

Accordingly, there continues to be a need in the art for sampling devices that are capable operating under a wide range of operating conditions and/or for sampling for the presence of a wide range of compounds, including both compounds of low volatility that require substantial heating to collect and compound of high volatility that are more effectively captured via whole air sampling.

BRIEF DESCRIPTION OF THE INVENTION

According to an exemplary embodiment, a sampling device for a substance detection instrument includes a membrane comprising a porous support having a coating thereon, the coating comprising a carborane polysiloxane or an arylene polysiloxane, the membrane having a front side configured to be placed in contact with a test sample and a back side;

a sample line having an inlet proximate to the back side of the membrane and an outlet in fluid communication with a substance detector; and a source of carrier gas in fluid communication with the back side of the membrane and the sample line inlet.

In another exemplary embodiment, the sampling device further includes a heater disposed to heat the membrane.

In yet another exemplary embodiment, a membrane for a sampling device includes a porous support having a coating thereon, the coating including a carborane polysiloxane or an arylene polysiloxane.

In a further exemplary embodiment, a method of sampling a material for the presence of substances comprises placing a sampling device in contact with the material, the sampling device comprising:

a membrane comprising a porous support having a coating thereon, said coating comprising a carborane polysiloxane or an arylene polysiloxane, said membrane having a front side configured to be placed in contact with a test sample and a back side;

a sample line having an inlet proximate to the back side of the membrane and an outlet in fluid communication with a substance detector; and a source of carrier gas in fluid communication with the back side of the membrane and the sample line inlet.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION OF THE INVENTION

Figure 1:
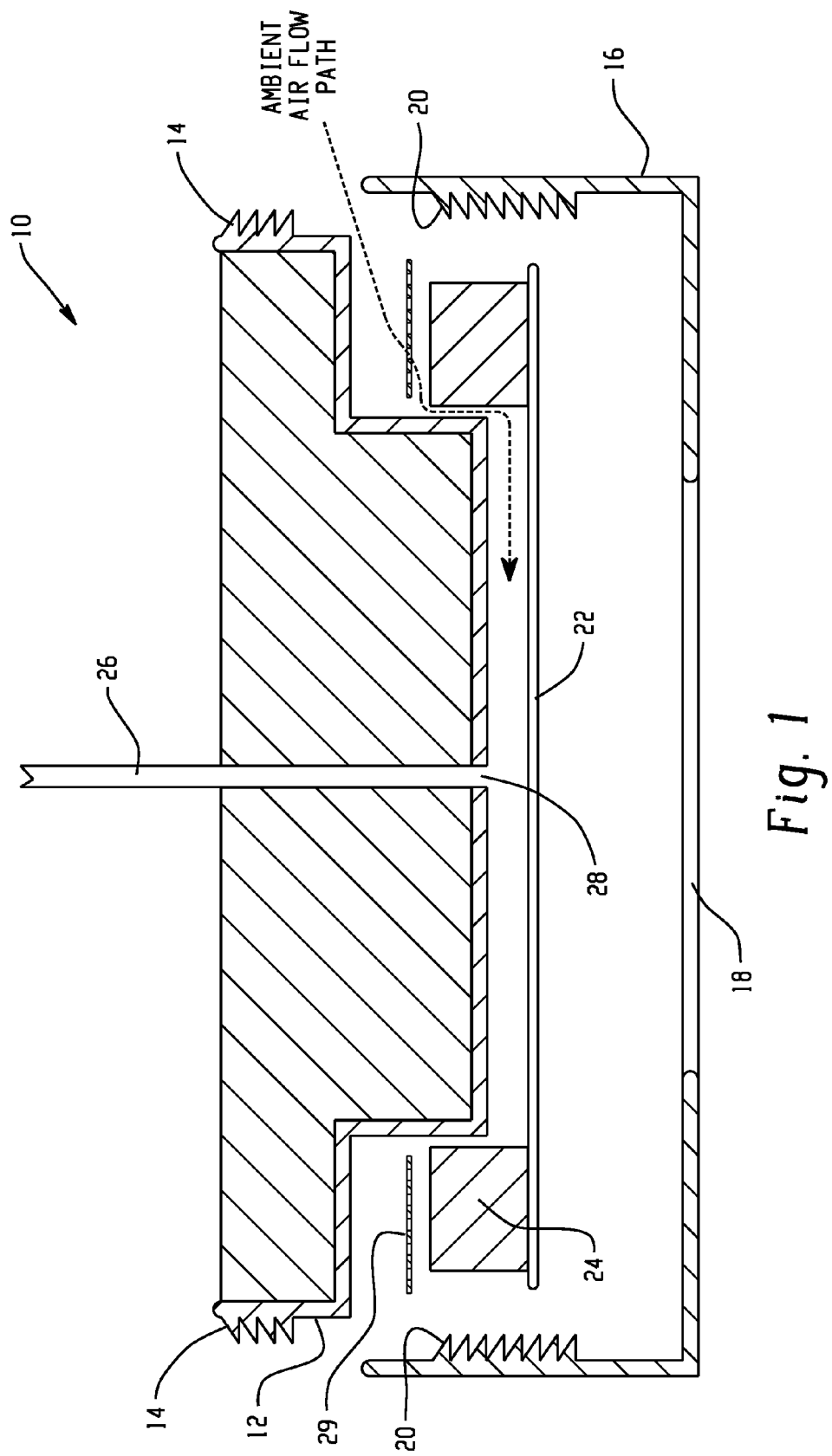
FIG. 1 depicts a schematic representation of a sampling device for a substance detection instrument.
Figure 2:
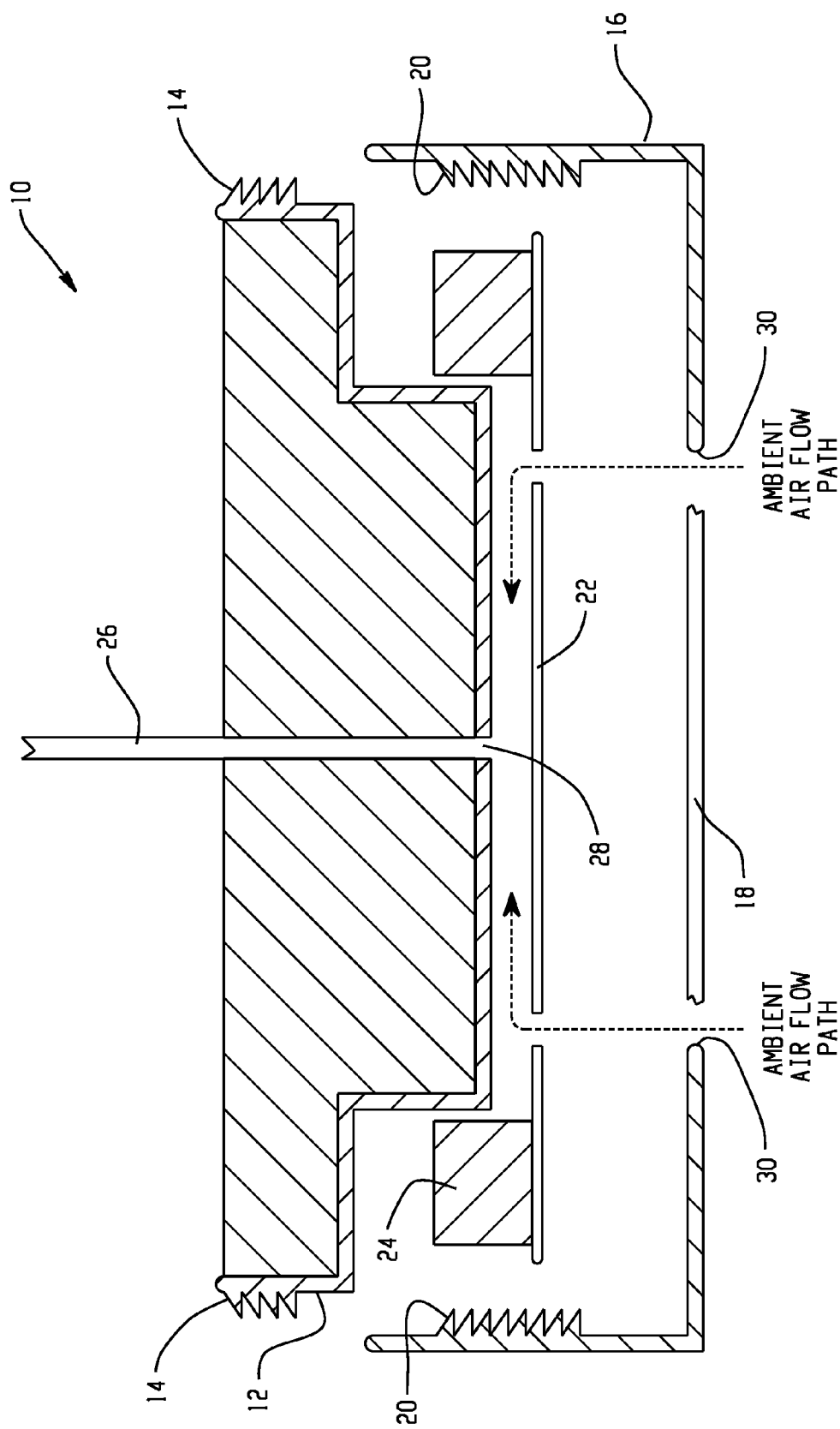
FIG. 2 depicts a schematic representation of an alternative embodiment of a sampling device for a substance detection instrument.

A simplified sampling device is schematically shown in an exploded cross-sectional view in FIG. 1, in which a sampling device 10 has a housing 12 having a threaded coupling or other similar attachment feature 14. A membrane retainer 16 having an opening 18 disposed therein is disposed over the housing 12 such that threaded coupling 20 on the retainer engages with threaded coupling 14 on the housing to secure the membrane retainer to the housing 12. Membrane 22 comprising a porous support having a coating thereon is supported by a membrane support ring 24 to maintain a carrier gas flow gap between the membrane 22 and the housing 12, and a sample transfer line 26 is disposed in the housing having an inlet 28 that is disposed proximate to the upper (rear) surface of the membrane 22 and an outlet (not shown) that leads to a substance detector (not shown) such as a mass spectrometer. During operation, a vacuum is drawn in the sample transfer line 26 by a pump, diaphragm, or other suitable gas transfer mechanism to draw sample gas from the inlet 28 to provide test gas to the substance detector. This creates a membrane sweep flow of ambient gas (e.g., air) drawn along the path shown in FIG. 1 through wire mesh washer 29. This membrane sweep flow carries volatilized molecules to the sample line inlet 28 from the test sample that have diffused through the membrane 22, from where they are transported to the substance detector. In an alternative embodiment as shown in FIG. 2, uncoated area(s) 30 in the membrane 22, disposed in the area of the retainer opening 18 proximate to the edge of the retainer opening provide an alternative flow path for carrier gas as shown in FIG. 2. In this alternative embodiment, mesh washer 29 (FIG. 1) is eliminated and the membrane support ring is disposed to provide a seal against housing 12 when the membrane 22 is in place.

Figure 3:
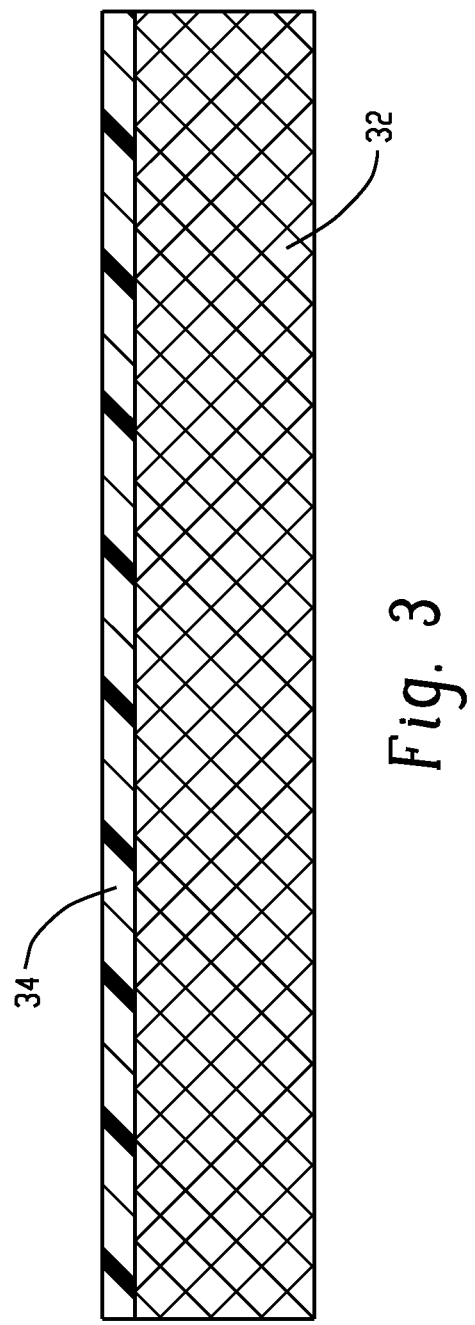
FIG. 3 depicts a schematic representation of a membrane for use in a sampling device for a substance detection instrument.

Turning now to FIG. 3, a schematic cross-section view of membrane 22 is shown having a porous support 32 having coating 34 thereon. The porous support can be fabricated from any sort of inert material, including but not limited to metals (e.g., nickel, chromium, stainless steel alloys such as SS304, SS306, SS316), quartz, glass, fiberglass, cloths composed of carbon nanotube fibers, polymers (e.g., fluoropolymers, polyamides, aramids), and the like as are known in the art and may be formed from woven clothes or sintered disks. The support is porous, and in an exemplary embodiment is a mesh support having mesh opening sizes ranging from 2 μm to 25 μm, more specifically 4 μm to 5 μm. The thickness of the support can vary depending on the specific design requirements and the properties of the coatings and the molecules being tested for, but can generally range from 50 μm to 205 μm. In the case of a sintered disk support, mechanical requirements would necessitate a support thickness of 1588±794 μm, though the membrane material per se would be the same thickness as if a wire cloth support were used.

In some exemplary embodiments, prior to applying the arylene or carborane siloxane coating, the support is surface treated to provide a coating comprising silicon or other inert surface layers such as silica ($SiO_2$), substituted silica, siloxane oligomers, and the like, any of which may be substituted with functional groups (e.g., alkyl, fluoroalkyl) to provide desired levels of inertness and/or hydrophobicity. Such surface treatments can improve the adhesion and integration of the siloxane coating, as well as modifying the characteristics of the membrane, e.g., hydrophobicity. Such surface treatments are known in the art, and generally involve applying silicon-containing surface coatings (e.g., carboxysilicons) using vapor deposition techniques such as chemical vapor deposition of silicon hydride gas. Other surface treatments include but are not limited to electropolishing (e.g., Summa® polishing) or anodization. Exemplary surface treatment techniques and compositions are disclosed, for example, in U.S. Pat. Nos. 6,444,326, 6,511,760, 7,867,627, and 7,070,833, the disclosures of which are incorporated herein by reference in their entirety. Surface-treatment processing is commercially available from suppliers such as Silcotek of Bellefonte, Pa. In an exemplary embodiment, a hydrophobic surface treatment such as Silcotek's Dursan™ surface treatment is utilized. In another exemplary embodiment, a hydrophobic surface treatment such as Silcotek's Dursan™ surface treatment is utilized in conjunction with the above-described exemplary embodiment where portion(s) of the support are not coated with the siloxane coating in order to provide a flow path for carrier gas. Surface treated supports of various morphologies are commercially available from suppliers such as Restek of Bellefonte, Pa.

In an exemplary embodiment, the sampling device's membrane is a porous support coated with a layer comprising an arylene polysiloxane. Arylene polysiloxanes are well-known in the polymer art, and include both arylene groups and siloxane groups in a polymer backbone. Arylene polysiloxanes can be characterized by the formula (I):

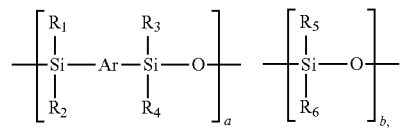

wherein $R_1$, $R_2$, $R_3$, $R_4$, $R_5$, and $R_6$ each independently represents an organic radical, Ar represents a divalent arylene radical, a represents 20 to 80 mole %, more specifically from 40 to 60 mole %, and b represents 80 to 20 mole %, more specifically from 60 to 40 mole %. Exemplary groups for $R_1$-$R_6$ can include substituted or unsubstituted alkyl of 1 to 6 carbon atoms and substituted or unsubstituted aryl of 6 to 20 carbon atoms. In a more specific exemplary embodiment each of $R_1$-$R_6$ is unsubstituted alkyl of 1 to 4 carbon atoms, and in a still more specific exemplary embodiment each of $R_1$-$R_6$ is a methyl group. As used herein in the definition of Ar, a divalent arylene radical includes any divalent radical comprising divalent arylene, including compound divalent radicals such as alkylenearylene. Exemplary groups for Ar include substituted or unsubstituted arylene (including alkylenearylene) of 6-20 carbon atoms. U.S. Pat. No. 5,346,980 (the disclosure of which is incorporated herein by reference in its entirety) discloses arylene polysiloxanes where Ar includes 1 to 3 rings that can be fused or joined by a covalent bond or —O— linkage, an ester linkage, a carbonate linkage, an —Si(R)$_2$— linkage. In a more specific exemplary embodiment, Ar is divalent phenyl. In another specific exemplary embodiment, Ar is a 1,4-divalent phenyl. Depending on available synthesis pathways, any of the $R_1$-$R_6$ and Ar groups can be substituted with functional or non-functional substituents, including but not limited to unsaturated C—C double bonds, halogen, oxirane, hydroxyl, and the like. Also, terminal silarylene and siloxane groups on the copolymer molecule can provide an active hydrogen (either a silyl hydrogen or siloxyl hydrogen) for attaching functional or non-functional substituents. The silarylene and siloxane groups in the above formula can be incorporated into the co-polymer in any pattern, including as random repeat units, or in blocks of from 2-100, more specifically from 2-50, which may themselves be blocks of a single monomer or blocks containing different monomers in either a random or block pattern. In a further exemplary embodiment, a and b add up to 100% including the molecular weight of any terminal atoms or groups; however, in some exemplary embodiments, other comonomers may be included so that a and b add up to less than 100%. In a more specific exemplary embodiment, a and b add up to 90-100%. Other co-monomers or block co-polymers can be included in co-polymer through, for example, through terminal ester or carbonate linkages to a silarylene or siloxane group. Various ratios of a:b may be utilized in the co-polymer. In some exemplary embodiments, the a:b ratio varies from 1.25:1 to 1:1.25, more specifically 1.1:1 to 1:1.1. Further exemplary embodiments, including substituents on polymers, synthesis techniques, and the like are disclosed in U.S. Pat. Nos. 3,167, 528, 3,959,403, US 2002/0013441 A1, and U.S. Stat. Inv. Reg. H1612, the disclosures of which are incorporated herein by reference in their entirety, and the above-referenced U.S. Pat. No. 5,346,980. Commercially available arylene polysiloxanes include DCS-8024 (silethylphenylene)/(dimethylsiloxane) copolymer available from Gelest, Inc. of Morrisville, Pa., and Gelest OE™ 43, a 2-part silicone RTV encapsulant of a (silethylphenylene)(dimethylsiloxane) copolymer in a 1:1 kit, also available from Gelest, Inc.

In another exemplary embodiment, the sampling device's membrane is a porous support coated with a layer comprising an carborane polysiloxane. Carborane polysiloxanes are well-known in the polymer art, and include both carborane groups and siloxane groups in a polymer backbone. Carborane polysiloxanes can be characterized by the formula (II):

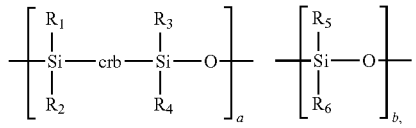

wherein $R_1$, $R_2$, $R_3$, $R_4$, $R_5$, and $R_6$, a, and b are as defined above, and crb represents a divalent carborane radical. As used herein in the definition of crb, a divalent carborane radical includes any divalent radical comprising divalent carborane, including compound divalent radicals such as alkylene-carborane-alkylene. Exemplary carborane groups include known carboranes such as 1,7-decacarborane, 1,12-decacarborane, 1,10-octacarborane, 1,6-octacarborane, 2,4-pentacarborane, 1,6-tetracarborane, 9-alkyl-1,7-decacarborane, 9,10-dialkyl-1,7-decacarborane, 2-alkyl-1,12-decacarborane, 2-alkyl-1,10-octacarborane, 8-alkyl-1,6-octacarborane, decachloro-1,7-decacarborane, decachloro-1,12-decacarborane, octachloro-1,10-octacarborane, decafluoro-1,7-decacarborane, decafluoro-1,12-decacarborane, octafluoro-1,10-octacarborane, or mixtures thereof. Depending on available synthesis pathways, any of the $R_1$-$R_6$ and crb groups can be substituted with functional or non-functional substituents, including but not limited to unsaturated C—C double bonds, halogen, oxirane, hydroxyl, and the like. Also, terminal groups on the copolymer molecule can provide an active hydrogen (either a silyl hydrogen or siloxyl hydrogen) for attaching functional or non-functional substituents. The groups in the above formula can be incorporated into the co-polymer in any pattern, including as random repeat units, or in blocks of from 2-100, more specifically from 2-50, which may themselves be blocks of a single monomer or blocks containing different monomers in either a random or block pattern. In a further exemplary embodiment, a and b add up to 100% including the molecular weight of any terminal atoms or groups; however, in some exemplary embodiments, other comonomers may be included so that a and b add up to less than 100%. Further exemplary embodiments, including substituents on polymers, synthesis techniques, and the like are disclosed in U.S. Pat. Nos. 4,145,504, 4,208,492, 4,235,987, 5,208,310, and US 2005/0171317, the disclosures of each of which is incorporated herein by reference.

Carborane siloxane and arylene siloxane polymers useful in the embodiments described herein can have molecular weights that range from 3000 to 125000, more specifically from 6000 to 25000, hardness values less than 100 (Shore A), and kinematic viscosity after curing of greater than or equal to 1000 cSt.

A layer of arylene polysiloxane or carborane polysiloxane can be applied as 2-part curable fluid composition to the porous support using any conventional coating technique such as brushing, rolling, dipping, and the like, and then cured. Typical curing conditions can vary depending on the specific materials involved, but in exemplary embodiments can range from 2 to 6 hours at elevated temperatures (e.g., 50-60° C.) to greater than 70 hours at room temperature. The layer should be sufficient to fill or bridge over the pores or mesh openings of the porous support, and can range from 25 μm to 300 μm thick, more specifically 50 μm to 200 μm.

The sampling device described herein can be used with any type detection device that is capable of detecting volatile molecules in a carrier gas sample or stream, including mass spectrometers or gas chromatographs, including devices with combined mass spectrometry and gas chromatography functions. Such devices, including various features and variations thereof, are well-known and are further described in Robert Grob & Eugene Barry, *Modern Practice of Chromatography—Fourth Ed.*, John Wiley & Sons, 2004, the disclosure of which is incorporated herein by reference in its entirety. Further detailed disclosure of such detection devices is not warranted, because the sampling device described herein is not limited to use with any particular type or design of detection device.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A sampling device for a substance detection instrument, comprising:
   a housing;
   a membrane retainer secured to the housing;
   a membrane comprising a porous mesh support having mesh opening sizes of 2 μm to 25 μm or a porous sintered disk support, having a coating thereon, said coating comprising a carborane polysiloxane or an arylene polysiloxane, said membrane having a front side configured to be placed in contact with a test sample and a back side;

a sample line having an inlet in the housing proximate to the back side of the membrane and an outlet in fluid communication with a substance detector; and a source of carrier gas in fluid communication with the back side of the membrane and the sample line inlet.

2. The sampling device of claim 1, further comprising a heater disposed to heat the membrane.

3. A substance detection instrument comprising the sampling device of claim 1 and the substance detector, wherein the substance detector comprises a mass spectrometer.

4. A substance detection instrument comprising the sampling device of claim 1 and the substance detector, wherein the substance detector comprises a gas chromatography detector.

5. A substance detection instrument comprising the sampling device of claim 1 and the substance detector, wherein the substance detector comprises a gas chromatography detector and a mass spectrometer.

6. The sampling device of claim 2, wherein the heater is controllable to variable temperature levels above 220° C.

7. The sampling device of claim 1, wherein the membrane comprises a porous mesh support having mesh opening sizes ranging from 2 μm to 25 μm.

8. The sampling device of claim 1, wherein the source of carrier gas comprises one or more openings or uncoated areas in the membrane through which ambient gas proximate to the sampling device can pass.

9. The sampling device of claim 1, wherein the porous support comprises an inert support material comprising thereon a layer comprising silicon between the inert support material and said coating.

10. The sampling device of claim 1, wherein said coating comprises an arylene polysiloxane.

11. The sampling device of claim 10, wherein the arylene polysiloxane is a copolymer comprising repeat units according to the formula:

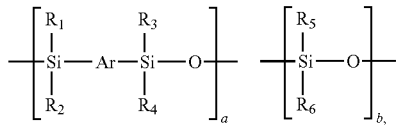

wherein $R_1$, $R_2$, $R_3$, $R_4$, $R_5$, and $R_6$ each independently represents an organic radical, a represents 20 to 80 mole %, and b represents 80 to 20 mole %.

12. The sampling device of claim 1, wherein the coating comprises a carborane polysiloxane.

13. The sampling device of claim 12, wherein the carborane polysiloxane is a copolymer comprising repeat units according to the formula:

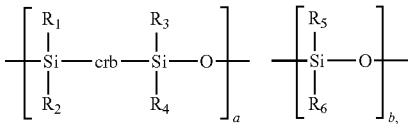

wherein $R_1$, $R_2$, $R_3$, $R_4$, $R_5$, and $R_6$ each independently represents an organic radical, R' and R" each independently represents a divalent organic linking group, crb represents a divalent carborane radical, a represents 20 to 80 mole %, and b represents 80 to 20 mole %.

14. The sampling device of claim 1, wherein the membrane comprises a porous sintered disk support.

15. The sampling device of claim 8, wherein the source of carrier gas comprises one or more openings in the membrane through which ambient gas proximate to the sampling device can pass.

16. The sampling device of claim 8, wherein the source of carrier gas comprises one or more uncoated areas in the membrane through which ambient gas proximate to the sampling device can pass.

17. A method of sampling a material for the presence of substances with a sample device comprising: a housing; a membrane retainer secured to the housing; and a membrane comprising a porous mesh support having mesh opening sizes of 2 μm to 25 μm or a porous sintered disk support having a coating thereon, said coating comprising a carborane polysiloxane or an arylene polysiloxane, said membrane having a front side, a back side, and a sample line having an inlet in the housing proximate to the back side of the membrane and an outlet in fluid communication with a substance detector, the method comprising placing the front side of the membrane in contact with the material flowing a carrier gas in fluid communication with the back side of the membrane to receive volatile molecules from the material that have diffused through the membrane and carry them into the sample line inlet.

* * * * *